United States Patent
Zhang et al.

(10) Patent No.: US 9,540,682 B2
(45) Date of Patent: Jan. 10, 2017

(54) DOUBLE-STRANDED NUCLEIC ACID, USE AND KIT THEREOF IN RIBONUCLEASE DETECTION

(75) Inventors: Hongyan Zhang, Jiangsu (CN); Weiyan Huang, Beijing (CN)

(73) Assignee: Suzhou Ribo Life Science Co., Ltd., Kunshan (CN)

( * ) Notice: Subject to any disclaimer, the term of this patent is extended or adjusted under 35 U.S.C. 154(b) by 400 days.

(21) Appl. No.: 14/346,282

(22) PCT Filed: Sep. 10, 2012

(86) PCT No.: PCT/CN2012/081166
§ 371 (c)(1),
(2), (4) Date: Jul. 9, 2014

(87) PCT Pub. No.: WO2013/040992
PCT Pub. Date: Mar. 28, 2013

(65) Prior Publication Data
US 2015/0037805 A1    Feb. 5, 2015

(30) Foreign Application Priority Data

Sep. 20, 2011  (CN) .......................... 2011 1 0280177
Sep. 20, 2011  (CN) .......................... 2011 1 0280179

(51) Int. Cl.
| | | |
|---|---|---|
| C07H 21/02 | (2006.01) | |
| G01N 33/53 | (2006.01) | |
| C12Q 1/68 | (2006.01) | |
| C12Q 1/34 | (2006.01) | |
| G01N 33/574 | (2006.01) | |
| G01N 33/542 | (2006.01) | |

(52) U.S. Cl.
CPC .............. *C12Q 1/6818* (2013.01); *C12Q 1/34* (2013.01); *C12Q 1/6886* (2013.01); *G01N 33/542* (2013.01); *G01N 33/57496* (2013.01); *G01N 2333/922* (2013.01)

(58) Field of Classification Search
None
See application file for complete search history.

(56) References Cited

U.S. PATENT DOCUMENTS

| 5,786,139 A | 7/1998 | Burke et al. |
| 2003/0096286 A1 | 5/2003 | Crooke |
| 2004/0137479 A1 | 7/2004 | Walder et al. |
| 2007/0122804 A1 | 5/2007 | Fu |

FOREIGN PATENT DOCUMENTS

| CN | 101851618 A | 10/2010 |
| CN | 101851619 A | 10/2010 |

OTHER PUBLICATIONS

Chen, Zhongliang et al., A Modified Method for Measuring Serum Ribonuclase, Chongqing Medical Journal, Dec. 31, 1988, vol. 17, No. 6, pp. 3-6, ISSN 1671-8348.
James, D.D. et al., A Fluorescence-Based Assay for Ribonuclease A Activity, Analytical Biochemistry, Nov. 1, 1998, vol. 264, No. 1, pp. 26-33, ISSN 0003-2697.
Kunitz, M., A Spectrophotometric Method for The Measurement of Ribonuclease Activity, Journal of Biological Chemistry, (http://www.jbc.org/content/164/2/563.citation), 1946, vol. 164:563-568.
Zelenko, O. et al., A Novel Flurogenic Substrate for Ribonucleases. Synthesis and Enzymatic Characterization, Oxford University Press: Nucleic Acids Research, 1994, vol. 22, No. 14, pp. 2731-2739.
Si-Ping, Da., et al., Clinical Value of Serum Human Pancreatic Elastase 1 Level and Ribonuclease Activity in Patients with Pancreatic Diseases, Hospital, Third Military Medical University, 2001, vol. 23, No. 1, pp. 112-113.
Kelemen, B., et al., Hypersensitive Substrate for Ribonucleases, Oxford University Press: Nucleic Acids Research, 1999, vol. 27, No. 18, pp. 3696-3701.
International Search Report for PCT/CN2012/081166 mail dated Dec. 13, 2012.
International Searching Authority Written Opinion for PCT/CN2012/081166 mail dated Dec. 13, 2012.

*Primary Examiner* — James Martinell
(74) *Attorney, Agent, or Firm* — Nixon Peabody LLP

(57) ABSTRACT

Provided are a double-stranded nucleic acid and use thereof in ribonuclease detection, and a ribonuclease detection method and use thereof in tumor detection and/or diagnosis. Specifically, a double-stranded nucleic acid substrate comprises at least one ribonuclease sensitive site. The activity and content of the ribonuclease in a sample are detected by analyzing the degradation of the double-stranded nucleic acid substrate by the ribonuclease. Also provided are a ribonuclease detection kit and a tumor detection kit.

22 Claims, 3 Drawing Sheets

DOUBLE-STRANDED NUCLEIC ACID, USE AND KIT THEREOF IN RIBONUCLEASE DETECTION

CROSS-REFERENCE TO RELATED APPLICATIONS

This application is an U.S. national stage of PCT/CN2012/081166, filed on Sep. 10, 2012, which claims priority to Chinese Patent Application No. 201110280177.8, filed on Sep. 20, 2011 and Chinese Patent Application No. 201110280179.7, filed on Sep. 20, 2011, the contents of which are each incorporated herein by reference in its entirety.

SEQUENCE LISTING

The sequence listing of the present application has been submitted electronically via EFS-Web as an ASCII formatted sequence listing with a file name "SL_14346282", creation date of Sep. 2, 2016 and a size of 9,392 bytes. The sequence listing submitted via EFS-Web is part of the specification and is herein incorporated by reference in its entirety.

FIELD OF THE INVENTION

The present invention relates to the field of molecular biology. Specifically, the present invention relates to a double-stranded nucleic acid and its use in the detection of ribonuclease (RNase), an RNase detection method and its use in tumor detection and/or diagnosis, as well as an RNase detection kit and a tumor detection kit.

BACKGROUND OF THE INVENTION

Ribonuclease (RNase, also known as RNA enzyme) is a large category of enzyme which includes dozens of types of enzymes capable of hydrolyzing RNA substrates into small molecular nucleic acids. According to the location of the cleavage site, these enzymes can be divided into two classes: endoribonuclease and exoribonuclease, belonging to a plurality of subclasses within EC 2.7 (phosphorylase) and EC 3.1 (hydrolase), respectively. RNases of different sources have different specificities and modes of action. For example, the catalysate of RNase T1 is mononucleotide, and oligonucleotide consisting of 3'-guanylic acid or carrying an end of 3'-guanylic acid, while the catalysate of RNase T2 is mononucleotide, and oligonucleotide consisting of 3'-adenylic acid or carrying an end of 3'-adenylic acid. Most RNases need divalent cations as cofactors (such as: $Ca^{2+}$, $Mg^{2+}$, and the like), so the activities thereof may be blocked by ethylenediaminetetraacetic acid (EDTA).

In laboratory studies, two main kinds of RNases are RNase A and RNase H. RNase H is an endoribonuclease which can specifically hydrolyze the phosphodiester bond on an RNA strand backbone complementary to a DNA strand, i.e., decompose the RNA strand in an RNA/DNA hybrid. However, this enzyme cannot digest single-stranded or double-stranded DNA. RNase A is another endonuclease which has been researched in details and has extensive applications. RNase A can hydrolyze RNA, whereas it does not function on DNA. RNase A effectively and specifically catalyzes the cleavage of phosphodiester bond on RNA strand backbone at 3'-end of pyrimidine nucleotide residues C and U to form oligonucleotides with 2',3'-cyclic phosphate derivatives, thus it can be used to remove RNA contaminant in DNA preparations.

In order to detect the activity or content of RNase in a sample, the researchers have established many technical solutions on the basis of analyzing substrate degradation. These solutions can be roughly classified into two categories: one uses heterogeneous RNA molecules as substrates, and the other uses artificially synthesized RNA molecules as substrates, oligoribonucleotides for example. Normally, the detection technique using artificially synthesized oligoribonuclec acids as substrates has higher sensitivity and higher specificity. Among these solutions, numerous detection techniques are artfully applied, including direct staining method, spectrophotometric method, colorimetric detection, cascade chromogenic method, isotope tracer technique, fluorescence polarization technique and fluorescence quenching technique.

The selection of detection means to a large extent decides the sensitivity and application scope of analytical techniques. For example, in order to detect whether an experimental reagent is contaminated by RNase, a very sensitive detection technique is needed to determine the existence of a minute amount of RNase in the experimental reagent, thereby avoiding degradation of the experimental sample. If the detection means is not sensitive enough, it will be unable to detect the existence of RNase with a minute amount but is sufficient to influence the experimental result and will directly result in failure of the experiment. On the contrary, if the detection means is too sensitive, it will exclude the reagents containing an extremely minute amount of RNase which does not suffice to influence the experimental result. Although such high sensitivity can guarantee accuracy of the experimental result, it meanwhile will raise difficulty and cost of the experiment. In actual practice, it is ideal that the detection sensitivity is in a range of 1-100 picogram/ml (pg/ml) RNase A, but the sensitivity of commercial detection reagents is in a range of 10-100 pg/ml RNase A at present. On the other hand, as the monitoring of RNase is a routine laboratory operation, the detection technique is required to have relatively high stability and be easy to operate.

Earlier RNase activity detection was established on Kunitz technique (Kunitz M., A spectrophotometric method for the measurement of ribonuclease activity. J. Biol. Chem., 1946, 164:563-568). In this technique, a heterogeneous RNA sample was added into a test sample, the change in absorbance value of the RNA sample at 300 nm was detected by spectrophotometric method, and the activity of RNase in the sample was calculated. Shortly afterwards, Oshima optimized this technique (Oshima T, Uenishi N and Imahori K. Simple assay methods for ribonuclease T1, T2, and nuclease PI. Anal. Biochem., 1976, 71:632-634). Generally, the sensitivity of this detection solution is not high and does not meet the requirements for RNase activity detection.

In another RNase activity detection solution, firstly polyacrylamide gel was used to separate the sample (Wilson C W. A rapid staining technique for detection of RNase after polyacrylamide gel electrophoresis. Anal. Biochem., 1969, 31:506-511). By bringing the RNase sample separated by the gel into contact with a heterogeneous RNA substrate followed by RNA staining, the degradation condition of the RNA substrate was analyzed, and then RNase activity was detected. Although this solution is simple in terms of concept, the implementation thereof is rather time-consuming, and its sensitivity is not high (only RNase I of one unit or more can be detected). In the modified version of this solution, by improving the gel separation technique, Karpetsky raised the detection sensitivity to a degree capable of detecting RNase A with an amount of no more than 100 pg (Karpetsky T P, Davie G E, Shriven K K and Levy C C. Use of polynucleotide/polyacrylamide-gel electrophoresis as a sensitive technique for the detection and comparison of ribonuclease activities. Biochem. J., 1980, 189: 277-284). Even so, the modified solution does not effectively shorten the detection time. As a result, the solution still does not meet the need of experimental tests.

Another RNase activity detection solution was established by Egly and Kempf (Egly J M and Kempf J. Detection and estimation of very low ribonuclease activities in biological fluids. FEBS Letters, 1976, 63:250-254). By using RNase to degrade insoluble substrate and analyzing the nucleotides labeled by $^{125}$Iodine generated from degradation, the detection sensitivity of this solution may reach 0.01 pg/ml, which is suitable for applied in routine quality control and detection. However, as this technique adopts hazardous radioisotope, it is not suitable for routine use of ordinary laboratories or industries and its applicable scope is greatly restricted.

Another RNase activity detection technique was established by Wagner (Wagner A P, Iordachel M C and Wagner L P. A simple spectrophotometric method for the measurement of ribonuclease activity in biological fluids. J. Biochem. Biophys. Methods, 1983, 8:291-297). Through binding RNA with Pyronine-Y, the maximum absorbance peak value of RNA was raised to 572 nm, and the degradation of RNA by RNase in the sample resulted in linear reduction of this absorbance. The sensitivity of this detection technique is around 2 ng/ml RNase A, not suitable for the detection of RNase activity.

Another RNase detection technique was established by Greiner-Stoeffele (Greiner-Stoeffele T, Grunow M and Hahn U. A general ribonuclease assay using methylene blue. Anal. Biochem., 1996, 240:24-28). The dye methylene blue was intercalated into high-molecular-weight RNA substrate to form a dye-RNA complex, and the degradation of the RNA substrate by RNase in the sample released the dye from the complex, resulting in reduction of the absorbance at 688 nm. This solution also has the problem of low sensitivity, with a lower detection limit of 25 ng/ml only, not meeting the need of detecting RNase activity in conventional samples.

Another RNase detection technique was established by Karn (Karn R C, Crisp M, Yount E A and Hodes M E. A positive zymogram method for ribonuclease. Anal. Biochem., 1979, 96:464-468). In this solution, upon utilizing the degradation of a synthesized substrate by RNase A, a series of cascade reactions occurred and finally a detectable blue substance was formed. This detection solution may detect 0.066 unit of RNase A (~100 ng), which does not meet the need of common RNase detection, either.

Another RNase detection technique was established by Witmer (Witmer M R, Falcomer C M, Weiner M P, Kay M S, Begley T P, Ganem B and Scheraga H A. U-3'-BCIP: a chromogenic substrate for the detection of RNase A in recombinant DNA expression systems. Nucleic Acids Res., 1991, 19:1-4). The main feature of this technique was the synthesis of an RNase substrate U-3'-BCIP which would release a reporter group under the action of RNase. The release of the reporter group was detected by spectrophotometer at 650 nm, thereby calculating the activity and content of RNase in the sample. This solution is simple and convenient, but it is still not sensitive enough.

Fluorescence quenching technique is a research technique widely applied in different fields of life science. For example, it has been used to detect the activity of protease (Yaron A, Carmel A and Katchalski-Katzir E. Intramolecularly quenched fluorogenic substrates for hydrolytic enzymes. Anal. Biochem., 95:228-235, 1979), detect the activity of DNA restriction endonuclease (Ghosh S S, Eis P S, Blumeyer K, Fearon K and Millar D P. Real time kinetics of restriction endonuclease cleavage monitored by fluorescence resonance energy transfer. Nucleic Acids Res., 1994, 22:3155-3159), detect the 5' exonuclease activity of DNA polymerase (Gelfand D H, Holland P M, Saiki R K and Watson R M. Homogeneous assay system using the nuclease activity of a nucleic acid polymerase. U.S. Pat. No. 5,210,015, 1993), detect specific nucleic acid sequences (Gelfand D H, Holland P M, Saiki R K and Watson R M. Homogeneous assay system using the nuclease activity of a nucleic acid polymerase. U.S. Pat. No. 5,210,015, 1993; Tyagi S, Kramer F R and Lizardi P M. Detectably labeled dual conformation oligonucleotide probes, assays and kits. U.S. Pat. No. 5,925,517, 1999; Livak K J, Flood S J A, Marmaro J and Mullah K B. Hybridization assay using self-quenching fluorescence probe. U.S. Pat. No. 5,876,930, 1999; Nazarenko I A, Bhatnagar S K, Winn-Deen E S and Hohman R J. Nucleic acid amplification oligonucleotides with molecular energy transfer labels and methods based thereon. U.S. Pat. No. 5,866,336, 1999; Nadeau J G, Pitner B, Linn C P and Schram J L. Detection of nucleic acids by fluorescence quenching. U.S. Pat. No. 5,958,700, 1999), and detect immunoreaction (Maggio E T. Chemically induced fluorescence immunoassay. U.S. Pat. No. 4,220,450, 1980). In a solution which applied fluorescence resonance energy transfer technique to detect the activity of hammerhead ribozyme, a synthetic oligoribonucleic acid substrate was used, wherein one end of the oligoribonucleic acid substrate was attached to a FAM fluorophore and the other end was attached to a TAMRA quencher (Hanne A, Ramanujam M V, Rucker R and Krupp G. Fluorescence resonance energy transfer (FRET) to follow ribozyme reactions in real time. Nucleosides and Nucleotides. 1998, 17:1835-1850).

In another technical solution, Zelenko et al synthesized a dinucleotide substrate, wherein one end thereof was attached to a fluorophore (O-aminobenzoic acid) and the other end was attached to a quencher (2,4-dinitroaniline) (Zelenko O, Neumann U, Brill W, Pieles U, Moser H E and Hofsteenge J. A novel fluorogenic substrate for ribonucleases: synthesis and enzymatic characterization. Nucleic Acids Res., 1994, 22:2731-2739). Cleavage of this substrate by RNase A allowed the fluorophore to be separated from the quencher, leading to an increase in the fluorescence reading of the reaction system. This solution is designed to investigate enzymatic kinetics of RNase A, which has certain limitations in detection sensitivity and is not suitable for the detection of RNase activity of conventional samples, either.

In another solution, James designed a 9-mer chimeric oligonucleotide for studying the enzymatic kinetics of RNase A. In the middle of this chimeric substrate there lied one uracil nucleotide, with deoxyribonucleotides flanking this uracil nucleotide. One end of the oligonucleotide was attached to a fluorophore and the other end was attached to a quencher (James D A and Woolley G A. A fluorescence-based assay for ribonuclease A activity. Anal. Biochem., 1998, 264:26-33). The flaw of this solution is that it can merely be used to study the activity of certain RNases that can cleave uracil nucleotide, and on the other hand, a sensitive fluorophotometer is needed.

In another solution, Kelemen et al reported another similar technique (Kelemen B R, Klink T A, Behlke M A, Eubanks S R, Leland P A and Raines R T. Hypersensitive substrate for ribonucleases. Nucleic Acids Res., 1999, 27:3696-3701). Same as the research solution of James, this solution can only detect RNases that can cleave uracil nucleotide and needs a fluorophotometer.

In another solution, Burke et al reported detecting the cleavage activity of RNase on a synthetic substrate by utilizing fluorescence polarization technique (Burke T J, Bolger R E, Checovich W J and Tompson D V. Method and kit for detecting nucleic acid cleavage utilizing a covalently attached fluorescent tag. U.S. Pat. No. 5,786,139, 1998). At present, commercial kits based on this technique are available in the market (PanVera Corporation Catalog 2000, Section 3.10. 545 Science Drive, Madison, Wis. 53711). Wilson et al further improved this technique and realized the goal of real-time detection (Wilson G M, Lu H, Sun H, Kennedy A and Brewer G. A fluorescence-based assay for 3'→5' exoribonucleases: potential applications to the study of mRNA decay. RNA, 2000, 6:458-464). However, this technique needs to use a fluorescence polarimeter that an ordinary laboratory does not have, impacting its extensive use.

Another commercial RNase activity detection kit is supplied by PanVera Corporation (PanVera Corporation Catalog 2000, Section 3.10. 545 Science Drive, Madison, Wis. 53711). Comparing with the fluorescence polarization solution, this technique has lower sensitivity.

Another commercial RNase activity detection kit is supplied by Ambion, Inc. This solution is based on an RNA substrate labeled by biotin, and detects RNase activity through common chromogenic reaction (Ambion, Inc. Catalog 1999, p104. 2130 Woodward Street, Austin, Tex. 78744.). Without RNase, the substrate can remain intact and turns blue in the chromogenic reaction; if the substrate is degraded by RNase in a sample, no blue reaction can be formed. This solution is labor intensive and is not suitable for high-throughput applications.

Another commercial RNase activity detection kit analyzes substrate degradation through gel electrophoresis (Mo Bio, Web Catalog, 2000). This solution involves multi-step reactions with heavy workload and is not suitable for routine detection.

To summarize, although the existing detection methods described above have made some progress in increasing sensitivity and accuracy for RNase activity detection, they all have some defects and are not suitable for being used as a universal means for detecting RNase activity in samples with high sensitivity. Related technical solutions still have much room for improvement.

SUMMARY OF THE INVENTION

In order to develop a more stable and more specific RNase detection substrate to increase detection sensitivity and specificity, the inventors made extensive and intensive research on the degradation process and mechanism of double-stranded RNA substrate by RNase, and unexpectedly discovered that most degradations took place at two sensitive sites of the double-stranded RNA substrate: CA/UG and UA/UA. On the basis of this research finding, the inventors accomplished the present invention.

In one aspect, the present invention provides a double-stranded nucleic acid which can be cleaved by RNase, wherein the length of the double-stranded nucleic acid is 7-30 base pairs, the base sequence of the first single strand of the double-stranded nucleic acid contains at least one CA base sequence or UA base sequence, the base sequence of the second single strand of the double-stranded nucleic acid contains UG base sequence or UA base sequence which is complementary to the CA base sequence or the UA base sequence in the first single strand, one end of the double-stranded nucleic acid is attached to an energy donor group, the other end of the double-stranded nucleic acid is attached to an energy acceptor group, and energy transfer can occur between the energy donor group and the energy acceptor group.

According to one embodiment of the present invention, the length of the double-stranded nucleic acid is 7-30 base pairs, preferably is 22, 23, 24, 25, 26, 27, 28, 29 or 30 base pairs; or preferably is 7, 8, 9, 10, 11, 12, 13, 14, 15, 16, 17, 18, 19, 20 or 21 base pairs, more preferably is 9, 10, 11, 12, 13, 14 or 15 base pairs, and still more preferably is 7, 8, 9, 10, 11, 12 or 13 base pairs.

According to one embodiment of the present invention, the base sequence of the first single strand of the double-stranded nucleic acid contains at least one CA base sequence, and the base sequence of the second single strand of the double-stranded nucleic acid contains UG base sequence which is complementary to the CA base sequence in the first single strand.

According to one embodiment of the present invention, the base sequence of the first single strand of the double-stranded nucleic acid contains at least one UA base sequence, and the base sequence of the second single strand of the double-stranded nucleic acid contains UA base sequence which is complementary to the UA base sequence in the first single strand.

According to one embodiment of the present invention, the second single strand and the first single strand of the double-stranded nucleic acid are perfectly complementary, and the base sequence of the first single strand of the double-stranded nucleic acid preferably is 5'-AUGAGCCUGAUUU (SEQ ID NO: 15), 5'-AUGAGCCUAAUUU (SEQ ID NO: 16), 5'-GGCUGCU (SEQ ID NO:17), 5'-GAAUGAGCU (SEQ ID NO:18), 5'-GAGUCAGC-UAATCUU (SEQ ID NO: 19) or 5'-UGGUAUGAGC-CUGAUUUUGAU (SEQ ID NO: 20), and more preferably is 5'-AUGAGCCUGAUUU (SEQ ID NO: 15).

According to one embodiment of the present invention, the double-stranded nucleic acid contains at least one deoxyribonucleotide group.

According to one embodiment of the present invention, the double-stranded nucleic acid contains at least one modified nucleotide group.

According to one embodiment of the present invention, the modified nucleotide group is a nucleotide group in which at least one of phosphate group, ribose group and base is modified, wherein the nucleotide group in which ribose group is modified is a nucleotide group in which 2'-hydroxy of the ribose group is modified, and the nucleotide group in which ribose group is modified preferably is a nucleotide group in which 2'-hydroxy of the ribose group is substituted by methoxy (2'-methoxy) or fluorine (2'-fluoro).

According to one embodiment of the present invention, the energy donor group and the energy acceptor group are located on the same nucleic acid single strand of the double-stranded nucleic acid, or located on different nucleic acid single strands. Preferably, the energy donor group and the energy acceptor group are located at 5'-ends of the two single strands, respectively. The energy donor group and the energy acceptor group may be covalently attached to the end of the nucleic acid single strand.

According to one embodiment of the present invention, the energy donor group is a fluorescence donor group and the energy acceptor group is a fluorescence acceptor group, wherein the fluorescence acceptor group preferably is a fluorescence quenching group.

The fluorescence donor group preferably is at least one selected from the group consisting of fluorescein group, tetrachlorofluorescein group, hexachlorofluorescein group, rhodamine group, tetramethylrhodamine group, Cy dye, Texas Red group, Bodipy dye group and Alexa dye group, more preferably is at least one selected from the group consisting of 6-carboxyfluorescein group, 5-tetrachlorofluorescein group, 5-hexachlorofluorescein group, 6-carboxy-x-rhodamine group, indodicarbocyanine and 6-carboxytetramethylrhodamine group.

Preferably, the fluorescence acceptor group is selected from nitrogen-substituted xanthene group, substituted or unsubstituted 4-(phenyldiazenyl)phenylamine group, and substituted or unsubstituted 4-(phenyldiazenyl) naphthylamine group. More preferably, the fluorescence acceptor group is at least one selected from the group consisting of 4-(4'-dimethylaminophenylazo)benzoic acid group, N,N'-dimethyl-N,N'-diphenyl-4-((5-t-butoxycarbonylaminopentyl) aminocarbonyl) piperidinylsulfonerhodamine group, 4',5'-dinitrofluorescein group, pipecolic acid amide group, 4-[4-nitrophenyldiazinyl]phenylamine group and 4-[4-nitrophenyldiazinyl]naphthylamine group.

According to another aspect, the present invention provides the use of the double-stranded nucleic acid described above in RNase detection, wherein the RNase includes, but is not limited to RNase I, RNase A and RNase H.

According to another aspect, the present invention provides the use of the double-stranded nucleic acid described above in the manufacture of RNase detection reagent, wherein the RNase includes, but is not limited to RNase I, RNase A and RNase H.

According to another aspect, the present invention provides an RNase detection method, including the following steps: 1) obtaining the double-stranded nucleic acid described above; 2) contacting the double-stranded nucleic acid in step 1) with a test sample, such that the double-stranded nucleic acid can be cleaved by the RNase possibly existing in the test sample; 3) detecting a product after said contacting in step 2), thereby detecting the RNase in the test sample.

According to another aspect, the present invention provides a quantitative RNase detection method, including the following steps: 1) obtaining the double-stranded nucleic acid described above; 2) contacting the double-stranded nucleic acid in step 1) with a test sample, such that the double-stranded nucleic acid can be cleaved by the RNase possibly existing in the test sample; 3) detecting the amount of a cleavage product in the product after said contacting in step 2), thereby detecting the content of the RNase in the test sample.

According to one embodiment of the present invention, the cleavage product or the amount thereof is detected by measuring a fluorescence signal with a specific wavelength emitted by the energy donor group and/or the energy acceptor group attached to both ends of the double-stranded nucleic acid.

According to one embodiment of the present invention, the test sample is at least one of blood, plasma, serum, saliva, tissue fluid and urine sample.

According to one embodiment of the present invention, the method for detecting the cleavage product may include direct detection method and indirect detection method. The direct detection method refers to directly detect the change of the double-stranded nucleic acid substrate before and after contact with the sample. Particularly, such methods include, but are not limited to electrophoresis method, hybridization method and high performance liquid chromatography (HPLC) method. The indirect detection method refers to detect the change of the double-stranded nucleic acid substrate before and after contact with the sample by utilizing indirect detection techniques. Particularly, such methods include, but are not limited to fluorescence resonance energy transfer method and/or fluorescence quenching method.

According to another aspect, the present invention also provides the use of the detection methods described above in tumor detection and/or diagnosis.

According to one embodiment of the present invention, the tumor is gastric cancer, colon cancer or lung cancer.

The present invention also provides an RNase detection kit, which contains an effective amount of the double-stranded nucleic acid described above. Preferably, the kit further contains an RNase standard. The standard, i.e., a positive control, is a known substance with RNase activity.

The present invention also provides a tumor detection kit, which contains an effective amount of the double-stranded nucleic acid described above. Preferably, the kit further contains an RNase standard. The standard, i.e., a positive control, is a known substance with RNase activity.

By using the double-stranded nucleic acid substrate and the RNase detection method provided by the present invention, the activity and content of RNase in the samples of different sources can be sensitively and accurately detected. The RNase detection method provided by the present invention not only can be easily performed but also greatly reduces detection cost, exhibiting a considerably high use value in large-scale applications such as early detection, therapeutic effect evaluation and general survey of people for various diseases. Compared to the prior art, the double-stranded nucleic acid substrate and the RNase detection method provided by the present invention have obvious technical advantage, specifically reflected in the following aspects.

1) Substrate stability: Compared to the single-stranded RNA substrate in the prior art, the double-stranded nucleic acid substrate provided by the present invention shows higher stability, and has more significant technical advantage in practical application.
2) High specificity: The present invention is established and accomplished on the basis of analyzing RNase cleavage-sensitive sites in the RNA substrate. By utilizing the identified RNase cleavage-sensitive sites, the present invention can achieve specific detection of RNase and enhance the specificity and accuracy of detection.
3) Quantitative detection technique: On the basis of the two outstanding technical characteristics of the present invention, i.e., substrate stability and high specificity, the detection solution provided by the present invention can more stably detect the activity of RNase in a sample and further calculate the content of RNase, thereby establishing a feasible technique for quantitative detection of RNase, contributing a major development and advancement to existing detection technique.
4) High-throughput detection technique: The method using fluorescence resonance energy transfer technique to detect the activity and content of RNase in a sample provided by the present invention is easy to perform and is suitable for serving as a standard detection method, thereby carrying out high-throughput and low-cost detection for a large quantity of samples.
5) Broad applicability: The double-stranded nucleic acid substrate and the RNase detection method provided by the present invention may be used to establish a standard RNase detection system, and may be used to analyze and compare the activity and content of different RNases in-samples or between-samples.

DETAILED DESCRIPTION OF THE INVENTION

Figure 1:
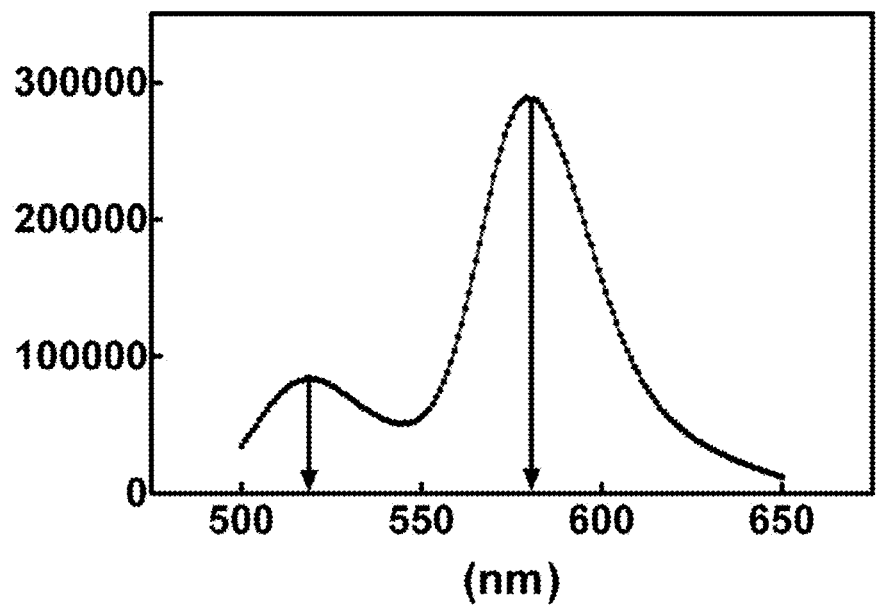
FIG. 1 is a fluorescence spectrum in the range of 500-650 nm of a reaction system before RNase A treatment according to one embodiment of the present invention.

In the present invention, fluorescence resonance energy transfer (FRET) refers to a phenomenon that, when the fluorescence spectrum of a fluorescence group (also known as fluorescence donor group) overlaps with the excitation spectrum of another fluorescence group (also known as fluorescence acceptor group), the excitation of the fluorescence donor group can induce the fluorescence acceptor group to emit fluorescence, while the fluorescence intensity of the fluorescence donor molecule itself decays. The generation and efficiency of FRET are closely related to the spatial distance between the fluorescence donor group and the fluorescence acceptor group. When this spatial distance is 7-10 nm, the efficiency of FRET is optimal. As the distance increases, FRET declines significantly. The efficiency of FRET between the fluorescence donor group and the fluorescence acceptor group may be reflected by $E=1/1+(R/R_0)^6$, where R stands for the distance between the fluorescence donor group and the fluorescence acceptor group, and $R_0$ stands for Förster distance. At Förster distance $R_0$, the efficiency of FRET between the fluorescence donor group and the fluorescence acceptor group is 50%. Förster distance $R_0$ relies on the overlapping degree between the donor emission spectrum and the acceptor excitation spectrum, and the relative orientation of the dipole for energy transfer between the donor and the acceptor.

It should be understood that, any fluorescence group combination with overlapped fluorescence emission spectrum and fluorescence excitation spectrum, i.e., any fluorescence group combination that can generate FRET phenomenon, can be applied in the present invention. These fluorescence group combinations include, but are not limited to the fluorescence group combinations mentioned in this Specification.

In the present invention, when a fluorescence quenching group is used as the fluorescence acceptor group, the fluorescence energy generated by exciting the fluorescence energy donor group is transferred via FRET to the fluorescence quenching group and then is absorbed and/or quenched by the fluorescence quenching group. In the present invention, the fluorescence quenching group used may be a quenching group which does not generate fluorescence itself (dark quenchers), or a fluorescence emission group which may generate fluorescence with a specific wavelength after energy absorption (fluorescent quenchers). When a fluorescence quenching method is used to detect RNase in a test sample, the RNase in the test sample will digest the double-stranded substrate of the present invention to physically separate the fluorescence donor group and fluorescence quenching group attached to both ends of the double-stranded substrate, and release a fluorescence signal of the fluorescence donor group absorbed and/or quenched by the fluorescence quenching group. In other words, when a fluorescence quenching group is used as the fluorescence acceptor group, after the double-stranded nucleic acid substrate is digested by the RNase in the test sample, the fluorescence signal of the fluorescence donor group will be enhanced. Therefore, by measuring the intensity of the fluorescence signal of the fluorescence donor group, RNase in the test sample can be detected qualitatively and/or quantitatively.

In the present invention, the fluorescence quenching group includes, but is not limited to 4-(4'-dimethylaminophenylazo)benzoic acid group, N,N'-dimethyl-N,N'-diphenyl-4-((5-t-butoxycarbonylaminopentyl)aminocarbonyl) piperidinylsulfonerhodamine group, 4',5'-dinitrofluorescein group, pipecolic acid amide group, 4-[4-nitrophenyldiazinyl]phenylamine group and 4-[4-nitrophenyldiazinyl]naphthylamine group. Anyway, any group that can absorb and/or quench the fluorescence energy generated by exciting the fluorescence donor group may be used in the present invention, but it is preferred to choose the quenching groups which themselves do not generate fluorescence (dark quenchers) as the fluorescence quenching groups of the present invention.

In the present invention, methods for modifying double-stranded nucleic acids are known to those skilled in the art. For example, the chemical modification of the double-stranded nucleic acid in the present invention is one chemical modification or a combination of more than one chemical modifications selected from the following:

(1) Modification of phosphodiester bond connecting nucleotides in the backbone structure of the double-stranded nucleic acid;

(2) Modification of ribose in the backbone structure of the double-stranded nucleic acid;

(3) Modification of base in the nucleotide residue of the double-stranded nucleic acid.

The modification of phosphodiester bond refers to modification of oxygen in the phosphodiester bond, including phosphorthioate modification and boranophosphate modification. As shown in the following formulae, the oxygen in the phosphodiester bond is replaced by sulfur and borane, respectively. Both modifications can stabilize the structure of RNA molecules and maintain high specificity and high affinity of base pairing.

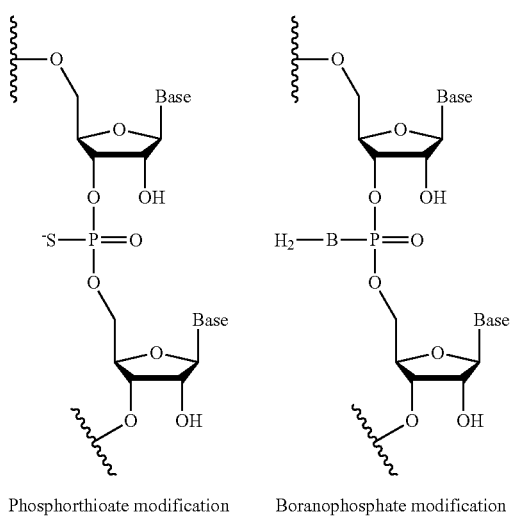

Phosphorthioate modification    Boranophosphate modification

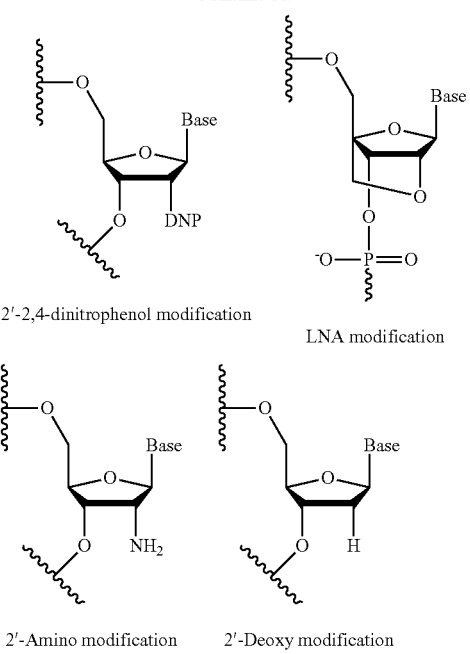

2'-2,4-dinitrophenol modification    LNA modification

2'-Amino modification    2'-Deoxy modification

The modification of ribose refers to modification of 2'-hydroxy (2'-OH) in the pentose of the nucleotide. Upon introducing certain substituents like methoxy or fluoro at 2'-hydroxy position of the ribose, RNase in serum cannot easily recognize small interfering nucleic acid, thereby enhancing the stability of the small interfering nucleic acid and allowing the small interfering nucleic acid to have stronger resistance against nuclease hydrolysis. The modification of 2'-hydroxy in the pentose of the nucleotide includes 2'-fluoro modification, 2'-methoxy modification, 2'-methoxyethoxy modification, 2'-2,4-dinitrophenol modification (2'-DNP modification), LNA modification, 2'-Amino modification, 2'-Deoxy modification, and the like.

The modification of base refers to modification of the base of the nucleotide. For example, 5'-bromo-uracil modification and 5'-iodo-uracil modification with bromine or iodine being introduced at 5-position of uracil are common modification methods for base. Modifications such as N3-methyl-uracil modification, 2,6-diaminopurine modification are also available.

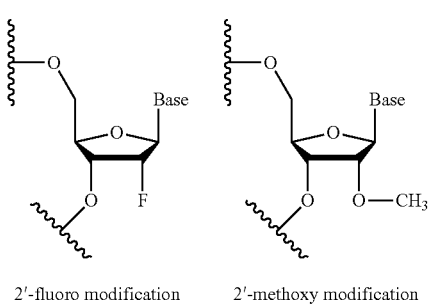

2'-fluoro modification    2'-methoxy modification

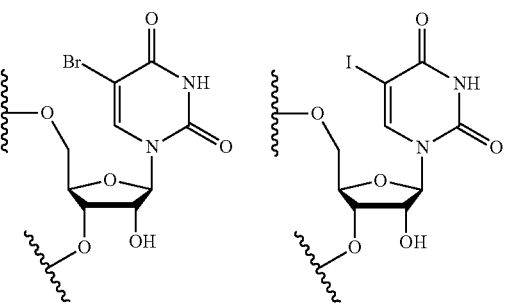

5'-bromo-uracil    5'-iodo-uracil

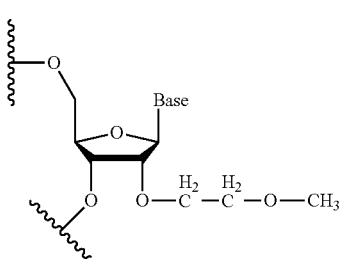

2'-methoxyethoxy modification

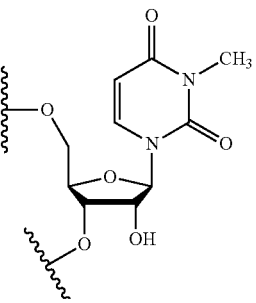

N3-methyl-uracil

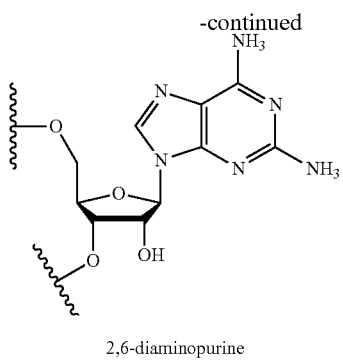

2,6-diaminopurine

Preferably, the modification is a modification of 2'-hydroxy of ribose in the backbone structure of the double-stranded nucleic acid. More preferably, the modification is the one where 2'-hydroxy of ribose in the backbone structure of the double-stranded nucleic acid is substituted by methoxy (2'-methoxy) or fluorine (2'-fluoro).

In the present invention, the method to detect RNase in a sample by using double-stranded nucleic acid substrate may be a direct or indirect detection method. The direct detection of degradation and cleavage product of a double-stranded nucleic acid substrate may be performed by electrophoresis method, hybridization method, HPLC method, and the like. All these methods may be implemented through routine operation and analytical procedures. For example, when HPLC method is adopted, through qualitative or quantitative analysis of a product generated after contacting the double-stranded nucleic acid substrate with a test sample, whether the test sample contains RNase may be decided or the RNase in the test sample may be quantitatively determined.

The indirect detection method mentioned in the present invention includes the method to detect RNase by FRET method. Particularly, this method includes the following steps: step 1): obtaining the double-stranded nucleic acid of the present invention, wherein the double-stranded nucleic acid is a linear double-stranded nucleic acid, its length may be 7-30 base pairs, one end of the double-stranded nucleic acid is attached to a fluorescence donor group, while the other end of the double-stranded nucleic acid is attached to a fluorescence acceptor group, and energy transfer can occur between the fluorescence donor group and the fluorescence acceptor group; step 2): contacting the double-stranded nucleic acid in step 1) with a test sample, such that the double-stranded nucleic acid can be cleaved by the RNase possibly existing in the test sample; step 3): detecting a fluorescence signal with a specific wavelength emitted by the fluorescence acceptor group, thereby qualitatively or quantitatively detecting the RNase in the test sample.

The indirect detection method mentioned in the present invention also includes the method to detect RNase by fluorescence quenching method. Particularly, this method includes the following steps: step 1): obtaining the double-stranded nucleic acid of the present invention, wherein the double-stranded nucleic acid is a linear double-stranded nucleic acid, its length may be 7-30 base pairs, one end of the double-stranded nucleic acid is attached to a fluorescence donor group, while the other end of the double-stranded nucleic acid is attached to a fluorescence quenching group, energy transfer can occur between the fluorescence donor group and the fluorescence quenching group, and the fluorescence energy generated by exciting the fluorescence donor group may be absorbed and/or quenched by the fluorescence quenching group; step 2): contacting the double-stranded nucleic acid in step 1) with a test sample, such that the double-stranded nucleic acid can be cleaved by the RNase possibly existing in the test sample; step 3): detecting a fluorescence signal with a specific wavelength emitted by the fluorescence donor group, thereby qualitatively or quantitatively detecting the RNase in the test sample.

EXAMPLES

Hereinafter the present invention will be further described in details in conjunction with the Examples. It should be understood that, these Examples are intended to illustrate but not to limit the scope of the present invention. Unless otherwise specified, all the reagents and culture media used in the present invention are commercial products. The experimental methods in which specific conditions are not indicated in the Examples are conducted according to conventional experimental methods, for example, the experimental methods described in "Molecular Cloning: A Laboratory Manual" edited by Sambrook et al (New York: Cold Spring Harbor Laboratory Press, 1989), or the experimental methods recommended by manufacturers.

Example 1

This example is intended to illustrate the sequence structures of the oligoribonucleotides and the optical parameters of the fluorescence groups used in the present invention. Guangzhou RiboBio Co., Ltd. was entrusted to synthesize a series of oligoribonucleotides. The fluorescence groups were labeled at the 5'-end of the oligoribonucleotides. Complementary oligoribonucleotides may be annealed following the method described in "Molecular Cloning: A Laboratory Manual" to form a double-stranded RNA. Table 1 shows the sequences of the synthesized oligoribonucleotides. Among these, for the oligoribonucleotide represented by SEQ ID NO: 11, the pentose of the guanylic acid residue at $3^{rd}$ position was modified by means of 2'-methoxy modification. For the oligoribonucleotide represented by SEQ ID NO: 12, the pentose of the uridylic acid residue at $14^{th}$ position was modified by means of 2'-fluoro substitution. For the oligoribonucleotide represented by SEQ ID NO: 13, the pentose of the cytidylic acid residue at $20^{th}$ position was modified by means of 2'-methoxy modification. Table 2 shows the optical parameters and the full names both in English and Chinese of the fluorescence groups used for labeling.

TABLE 1

Sequence structures of the oligoribonucleotides

| SEQ ID NO. | Nucleic acid sequences |
|---|---|
| SEQ ID NO: 1 | 5'-FAM-AUGAGCCU<u>G</u>AUUU |
| SEQ ID NO: 2 | 5'-TAMRA-AAAU<u>C</u>AGGCUCAU |
| SEQ ID NO: 3 | 5'-TET-AUGAGCCU<u>A</u>AUUU |
| SEQ ID NO: 4 | 5'-TAMRA-AAAU<u>U</u>AGGCUCAU |
| SEQ ID NO: 5 | 5'-HEX-GGCU<u>G</u>CU |
| SEQ ID NO: 6 | 5'-TAMRA-AG<u>C</u>AGCC |
| SEQ ID NO: 7 | 5'-FAM-GAAU<u>G</u>AGCU |
| SEQ ID NO: 8 | 5'-TAMRA-AGCU<u>CA</u>UUC |

TABLE 1-continued

Sequence structures of the oligoribonucleotides

| SEQ ID NO. | Nucleic acid sequences |
|---|---|
| SEQ ID NO: 9 | 5'-HEX-GAGU<u>C</u>AGC<u>UA</u>A<u>T</u>CUU |
| SEQ ID NO: 10 | 5'-TAMRA-AAGAU<u>UA</u>GC<u>UG</u>ACUC |
| SEQ ID NO: 11 | 5'-TET-UGG(OME)UAUGAGC<u>UG</u>AUUUGAU |
| SEQ ID NO: 12 | 5'-TAMRA-AUCAAAAUCAGGCU(F)CAUACCA |
| SEQ ID NO: 13 | 5'-FAM-AGCUGGUGG<u>UAC</u>AGAUGAUC(OME)UUGCA UCGUC |
| SEQ ID NO: 14 | 5'-TAMRA-GACGA<u>T</u>GCAAGAUCAUCUGUACCACC AGCU |

TABLE 2

Optical parameters of the fluorescence groups

| Abbr. | Full name in English; excitation wavelength; emission wavelength; color | Full name in Chinese |
|---|---|---|
| FAM | 6-carboxy-fluorescein; 494; 518; green | 6-羧基荧光素 |
| TET | 5-tetrachloro-fluorescein; 521; 538; orange | 5-四氯荧光素 |
| HEX | 5-hexachloro-fluorescein; 535; 553; pink | 5-六氯荧光素 |
| ROX | 6-carboxy-x-rhodamine; 587; 607; red | 6-羧基-x-罗丹明 |
| CYS | Indodicarbocyanine; 643; 667; bluish violet | N,N'-对羧苄基吲哚三菁 |
| TAMRA | tetramethyl-6-carboxyrhodamine; 560; 582; rosy | 6-羧基四甲基罗丹明 |
| DABCYL | 4-(4'-dimethylaminophenylazo)benzoic acid | 4-(4'-二甲基对胺基偶氮苯)苯甲酸 |

Example 2

This example is intended to illustrate the identification of FRET phenomenon of the present invention. In the technical solution provided by the present invention for detecting RNase level by FRET method, a critical condition is that FRET can take place between the fluorescence donor group and the fluorescence acceptor group labeled at the two ends of the double-stranded nucleic acid substrate.

Figure 2:
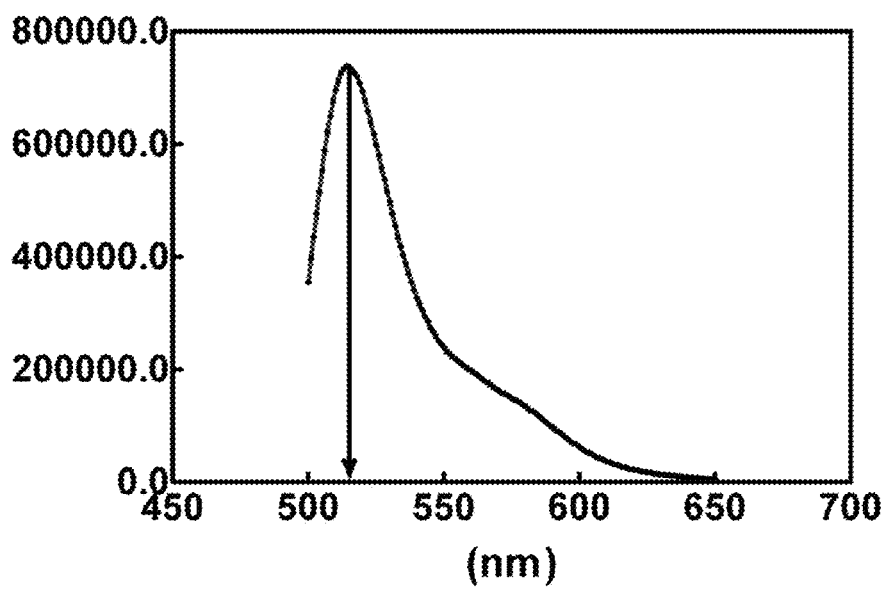
FIG. 2 is a fluorescence spectrum in the range of 500-650 nm of a reaction system after RNase A treatment according to one embodiment of the present invention.

In order to verify this fact, firstly oligoribonucleotide of SEQ ID NO: 1 (5'-FAM-AUGAGCCUGAUUU) and complementary oligoribonucleotide of SEQ ID NO: 2 (UA-CUCGGACUAAA-TAMRA-5') were annealed to form a double-stranded RNA substrate DS1. 4 µl DS1 was added to 2 ml FRET buffer solution (0.01 M Tris-HCl, pH 7.4, 0.002 M MgCl$_2$) and mixed, such that the final concentration of DS1 was 10 nM. Afterwards, the reaction system was added into a quartz detection cuvette of a fluorescence spectrometer, wherein micro-magnetic rotors were placed in the quartz cuvette. The quartz cuvette containing the reaction system was put into the fluorescence spectrometer. Excitation was set to be at 480 nm, and the spectral scanning range was 500-650 nm. The result is shown in FIG. 1, where the horizontal axis stands for wavelength and the vertical axis stands for fluorescence intensity. It can be seen that, the fluorescence intensity is low at 515 nm and is high at 575 nm. After 20 µl RNase A (the final concentration was 1×10$^{-6}$ µg/µl) was added to the reaction system, partial reaction substrates were degraded by RNase A, resulting in separation of the fluorescence donor group from the fluorescence acceptor group attached to these reaction substrates. At this time, the same spectral scanning was conducted. The obtained spectrogram is shown in FIG. 2, where the horizontal axis stands for wavelength and the vertical axis stands for fluorescence intensity. It can be seen that, the fluorescence intensity increases significantly at 515 nm, while substantially disappears and reduces to background level at 575 nm. This result indicates that, FRET indeed can occur between the fluorescence donor group and the fluorescence acceptor group attached to the double-stranded RNA substrate. On the other hand, this result also indicates that, after the substrate is degraded by the added RNase A, the distance between the fluorescence donor group and the fluorescence acceptor group is much greater than the maximum distance needed by FRET, so energy transfer cannot be carried out.

FRET of the following double-stranded substrates were detected according to the same detection method: the double-stranded substrate DS2 formed by annealing oligoribonucleotide of SEQ ID NO: 3 with oligoribonucleotide of SEQ ID NO: 4, the double-stranded substrate DS3 formed by annealing oligoribonucleotide of SEQ ID NO: 5 with oligoribonucleotide of SEQ ID NO: 6, the double-stranded substrate DS4 formed by annealing oligoribonucleotide of SEQ ID NO: 7 with oligoribonucleotide of SEQ ID NO: 8, the double-stranded substrate DS5 formed by annealing oligoribonucleotide of SEQ ID NO: 9 with oligoribonucleotide of SEQ ID NO: 10, the double-stranded substrate DS6 formed by annealing oligoribonucleotide of SEQ ID NO: 11 with oligoribonucleotide of SEQ ID NO: 12, and the double-stranded substrate DS7 formed by annealing oligoribonucleotide of SEQ ID NO: 13 with oligoribonucleotide of SEQ ID NO: 14. The results indicate that, FRET can take place between the fluorescence donor group and the fluorescence acceptor group attached to the two ends of all these substrates, so these double-stranded RNA substrates labeled with fluorescence groups may also be used in the RNase activity detection of the present invention.

Example 3

Figure 3:
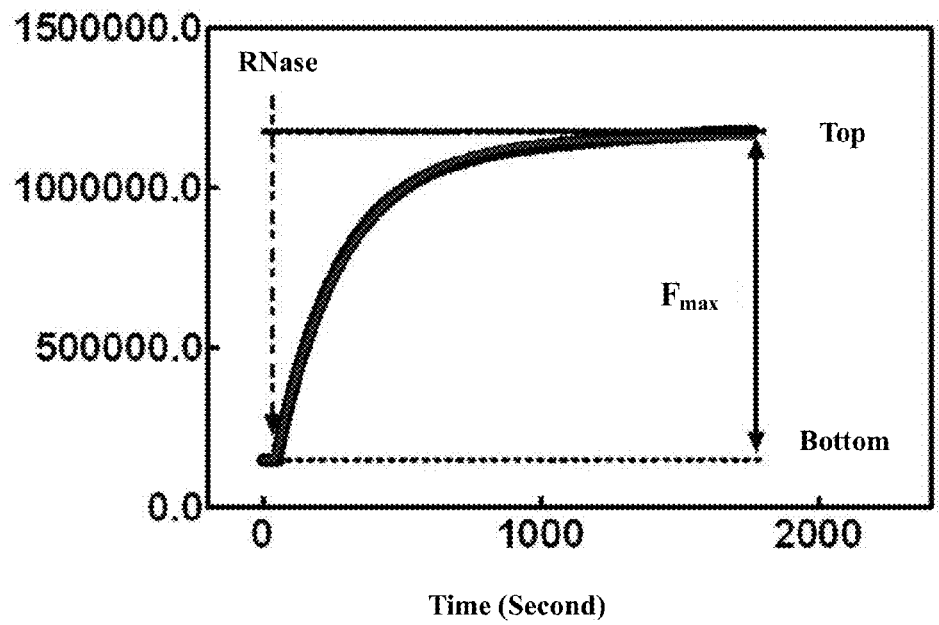
FIG. 3 is a detection time–fluorescence intensity curve during enzymatic reaction according to one embodiment of the present invention.

This example is intended to illustrate the method of the present invention for detecting RNase by FRET method. In order to detect the activity and content of RNase in a sample by FRET method, 4 µl double-stranded RNA substrate DS1 was added to 2 ml FRET buffer solution (0.01 M Tris-HCl, pH 7.4, 0.002 M MgCl$_2$) and mixed, such that the final concentration of DS1 was 10 nM. Afterwards, the reaction system was added into a quartz detection cuvette of a fluorescence spectrometer, wherein micro-magnetic rotors were placed in the quartz cuvette. After 20 µl RNase A at certain concentration was added to the reaction system, the reaction system was continuously excited at 480 nm and simultaneously detected at 515 nm to obtain fluorescence intensity values at an interval of second. By using these values, a time–fluorescence intensity curve was plotted. The result is shown in FIG. 3, where the horizontal axis stands for detection time and the vertical axis stands for fluorescence intensity. This curve conforms to the following enzymatic kinetics formula (I).

$$F = F_{max}(1 - e^{-K_{obs}(t+t0)})$$ Formula (I)

Where, $F_{max}$ is the maximum fluorescence intensity variation value generated when the fluorescence groups labeled at two ends of a double-stranded RNA substrate are completely separated after decomposition of the double-stranded RNA substrate, and may be determined through experiment. Experiments of a same batch only need to determine one $F_{max}$. t is time, and $t_0$ is the time point when RNase A is added after start of the experiment and may be 0. $K_{obs}$ is K value which describes reaction rate.

Afterwards, prism software was used to analyze this curve. Firstly, the curve was normalized based on the variation values of the fluorescence intensity after complete decomposition. Secondly, this normalized curve was subjected to nonlinear regression fitting with a range of 0~100%. After such fitting, K value correlated with the reaction rate may be obtained, and the goodness of fit between the fitted curve and the normalized reaction curve was as high as 0.99 or more. For relevant data analyzing process and formulae, the following two literatures may also be referred to.
1) Liu J Q, Chen C Y, Xue Y, Hao Y H and Tan Z. G-quadruplex hinders translocation of BLM helicase on DNA: a real-time fluorescence spectroscopic unwinding study and comparison with duplex substrates. J Am Chem Soc. 2010, 132(30):10521-7
2) Lucius A L, Wong C J and Lohman T M. Fluorescence stopped-flow studies of single turnover kinetics of *E. coli* RecBCD helicase-catalyzed DNA unwinding. J Mol Biol. 2004 339(4):731-50

Commercial RNase A at a known concentration was gradiently diluted with DEPC water. The diluted RNase A was used to treat a double-stranded RNA substrate with a final concentration of 10 nM and labeled with fluorescence groups at its two ends. The reaction temperature was 25° C. and the time duration was 900s. Through reactions between RNase A with a series of different concentrations and the substrate, a series of K values were obtained.

Figure 4:
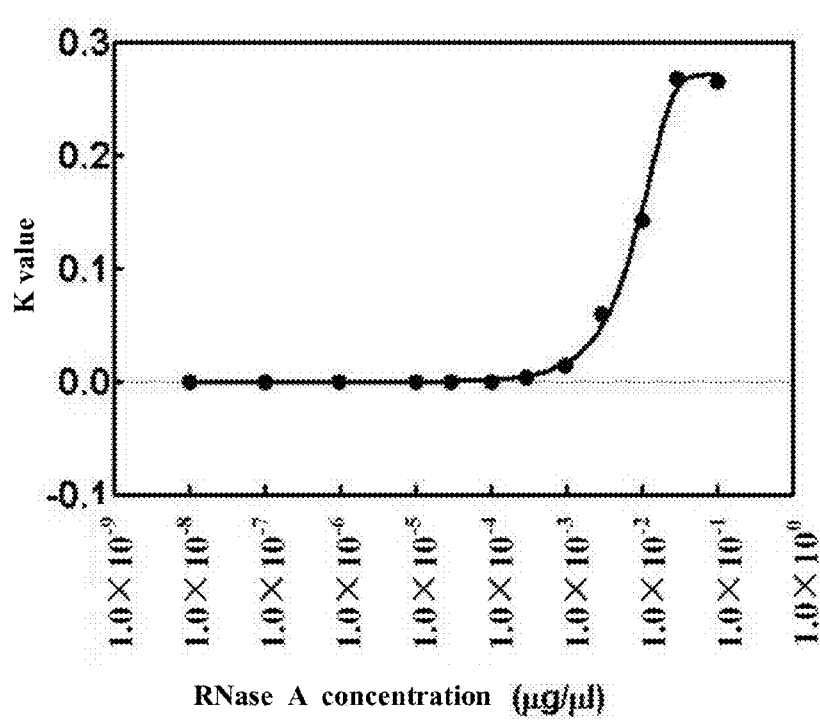
FIG. 4 is an RNase A concentration–K value curve according to one embodiment of the present invention.

The K values obtained from the above results and the corresponding concentrations were used to plot a standard curve expressing the relationship between RNase A concentration and K value. The result is shown in FIG. 4, where the horizontal axis stands for RNase A concentration and the vertical axis stands for K value determined at this concentration. This curve conforms to the following nonlinear regression fitting formula (II).

$$Y = Y_{min} + (Y_{max} + Y_{min})/(1 + 10^{(lgEC_{50} - lgX)^{K_H}}) \quad \text{Formula (II)}$$

Where, $Y_{max}$ is the maximum value of the curve, representing the K value corresponding to the maximum response of a sufficient amount of RNase A. $Y_{min}$ is the minimum value of the curve, representing the K value when RNase A activity is close to 0. X is RNase A concentration, $EC_{50}$ is the half maximal effective concentration, and $K_H$ is the slope of the linear section of the curve.

The relation of this curve conforms to dose accumulation effect. From this standard curve, the obtained K values may also be reversely regressed to corresponding RNase A concentrations. For relevant data analyzing process and formulae, the following two literatures may also be referred to.
1) Liu J Q, Chen C Y, Xue Y, Hao Y H and Tan Z. G-quadruplex hinders translocation of BLM helicase on DNA: a real-time fluorescence spectroscopic unwinding study and comparison with duplex substrates. J Am Chem Soc. 2010, 132(30):10521-7
2) Lucius A L, Wong C J and Lohman T M. Fluorescence stopped-flow studies of single turnover kinetics of *E. coli* RecBCD helicase-catalyzed DNA unwinding. J Mol Biol. 2004 339(4):731-50

The following double-stranded substrates were used for detecting RNase content in this example according to the same detection method: the double-stranded substrate DS2 formed by annealing oligoribonucleotide of SEQ ID NO: 3 with oligoribonucleotide of SEQ ID NO: 4, the double-stranded substrate DS3 formed by annealing oligoribonucleotide of SEQ ID NO: 5 with oligoribonucleotide of SEQ ID NO: 6, the double-stranded substrate DS4 formed by annealing oligoribonucleotide of SEQ ID NO: 7 with oligoribonucleotide of SEQ ID NO: 8, the double-stranded substrate DS5 formed by annealing oligoribonucleotide of SEQ ID NO: 9 with oligoribonucleotide of SEQ ID NO: 10, the double-stranded substrate DS6 formed by annealing oligoribonucleotide of SEQ ID NO: 11 with oligoribonucleotide of SEQ ID NO: 12, and the double-stranded substrate DS7 formed by annealing oligoribonucleotide of SEQ ID NO: 13 with oligoribonucleotide of SEQ ID NO: 14. The results indicate that, effective dose-accumulation curves can be obtained from all of these double-stranded RNA substrates, so these double-stranded RNA substrates may also be used to detect RNase activity.

Example 4

This example illustrates the method to quantitatively detect RNase in human serum by FRET method. Using the RNase detection methods given in Example 2 and Example 3, the activity and content of the RNase in human serum were analyzed. Specifically, oligoribonucleotide of SEQ ID NO: 1 and oligoribonucleotide of SEQ ID NO: 2 were annealed to from a double-stranded RNA substrate DS1. The human serum sample stored at −80° C. was taken out from a refrigerator and thawed on ice at low temperature. The thawed serum was centrifuged at 500×g for 10 min at 4° C. to remove the insoluble substances in the serum. The obtained supernatant was used to detect RNase content.

2 ml FRET buffer solution (0.01 M Tris-HCl, pH 7.4, 0.002 M $MgCl_2$) was taken, and DS1 was added thereinto at a final concentration of 10 nM. After mixed well, the reaction system was added into a quartz detection cuvette of a fluorescence spectrometer, wherein micro-magnetic rotors were placed in the quartz cuvette. 50 μl of the above prepared supernatant was added to the reaction system, and the reaction was performed at 25° C. with a reaction time of 900s. The reaction system was continuously excited at 480 nm and simultaneously detected at 515 nm to obtain fluorescence intensity values at an interval of second. These values were used to plot a time–fluorescence intensity curve, which was defined as the reaction curve. According to the same steps as described above, 50 μl of the above prepared supernatant was added to a reaction system only containing 2 ml FRET buffer solution without DS1. Reaction was performed at 25° C., and the obtained time–fluorescence intensity curve was defined as the background curve.

After the sampling points of the reaction curve and the background curve were aligned, by subtracting the corresponding fluorescence intensity value of the background curve at every time point from the fluorescence intensity value of the reaction curve, an actual reaction curve for analyzing RNase content was obtained. The actual reaction curve was normalized according to the variation values of the fluorescence intensity after complete reaction. Nonlinear fitting was conducted in the range of 0~100% to obtain K value representing reaction rate. Then, based on the previously obtained standard curve indicating the relationship between RNase A concentration and K value, RNase A concentration corresponding to K value was finally obtained through reverse regression. For relevant data analyzing process and formulae, the following two literatures may also be referred to.
1) Liu J Q, Chen C Y, Xue Y, Hao Y H and Tan Z. G-quadruplex hinders translocation of BLM helicase on DNA: a real-time fluorescence spectroscopic unwinding study and comparison with duplex substrates. J Am Chem Soc. 2010, 132(30):10521-7;
2) Lucius A L, Wong C J and Lohman T M. Fluorescence stopped-flow studies of single turnover kinetics of *E. coli* RecBCD helicase-catalyzed DNA unwinding. J Mol Biol. 2004 339(4):731-50

Example 5

This example is intended to illustrate detecting RNase content in clinical samples by the detection method of the present invention as well as the analysis result of the difference of RNase contents between healthy control individuals and tumor individuals.

Figure 5:
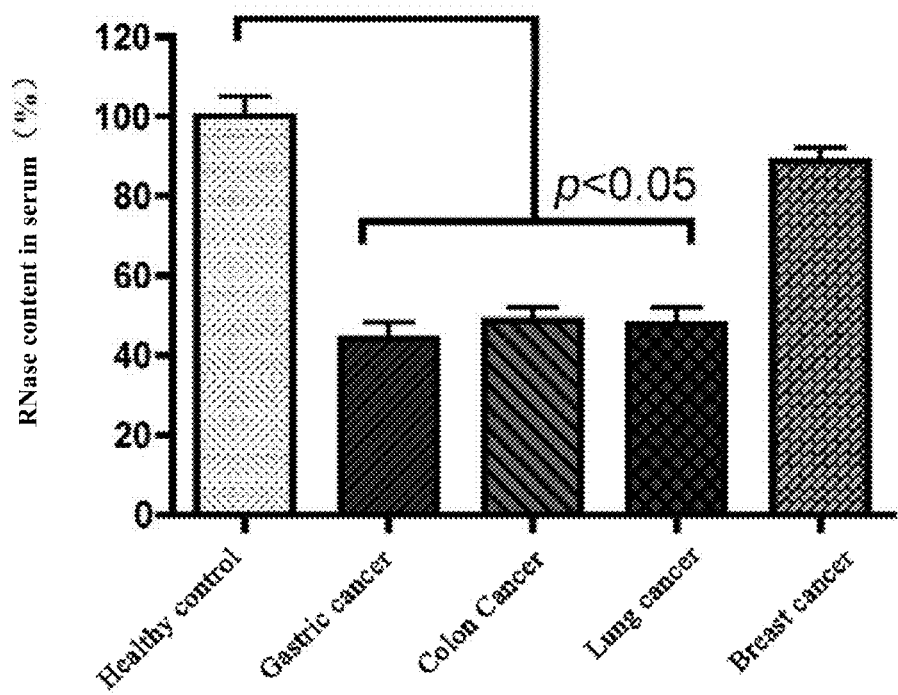
FIG. 5 is a comparison diagram of the RNase contents between healthy control individual and tumor individual samples according to one embodiment of the present invention.

2 ml serum was obtained from each of 18 gastric cancer patients, 20 colon cancer patients, 18 lung cancer patients and 19 breast cancer patients. Meanwhile, 2 ml control serum sample was obtained from each of the 24 healthy control individuals. FRET tests were carried out on these samples by the method described in Example 4 to obtain the concentration of RNase in each sample. Statistical analysis on RNase concentration of cancer patients was conducted by using the average value of the healthy control individuals as a benchmark. The result is shown in Table 3 and FIG. 5, wherein FIG. 5 is a comparison diagram of the RNase contents between healthy control individual and tumor individual samples, the horizontal axis indicates healthy control group and different tumor type group, and the vertical axis stands for RNase content in the serum sample of each tumor type normalized by using the average value of healthy control individuals. The result indicates that, compared to healthy control individuals, the RNase contents in the serum of gastric cancer, colon cancer and lung cancer patients are reduced by 30% or more. The result oft test shows that, P value of these differences is smaller than 0.05, demonstrating that there is significance, whereas the RNase content in the serum of breast cancer patients does not have significant change compared to that of the healthy control group.

TABLE 3

| Sample Type | Sample No. | RNase content (%) | Ratio relative to healthy control group (%) |
|---|---|---|---|
| Healthy control | 1 | 111.46 | — |
| Healthy control | 2 | 84.93 | — |
| Healthy control | 3 | 110.1 | — |
| Healthy control | 4 | 97.95 | — |
| Healthy control | 5 | 73.77 | — |
| Healthy control | 6 | 61 | — |
| Healthy control | 7 | 71.17 | — |
| Healthy control | 8 | 107.31 | — |
| Healthy control | 9 | 93.61 | — |
| Healthy control | 10 | 85.3 | — |
| Healthy control | 11 | 81.46 | — |
| Healthy control | 12 | 94.48 | — |
| Healthy control | 13 | 91.13 | — |
| Healthy control | 14 | 97.7 | — |
| Healthy control | 15 | 95.34 | — |
| Healthy control | 16 | 103.03 | — |

TABLE 3-continued

| Sample Type | Sample No. | RNase content (%) | Ratio relative to healthy control group (%) |
|---|---|---|---|
| Healthy control | 17 | 86.66 | — |
| Healthy control | 18 | 161.18 | — |
| Healthy control | 19 | 105.63 | — |
| Healthy control | 20 | 101.05 | — |
| Healthy control | 21 | 174.32 | — |
| Healthy control | 22 | 99.43 | — |
| Healthy control | 23 | 108.73 | — |
| Healthy control | 24 | 103.28 | — |
| Gastric cancer | 1 | 66.13 | 66 |
| Gastric cancer | 2 | 45.84 | 46 |
| Gastric cancer | 3 | 31.62 | 32 |
| Gastric cancer | 4 | 24.68 | 25 |
| Gastric cancer | 5 | 61.91 | 62 |
| Gastric cancer | 6 | 58.77 | 59 |
| Gastric cancer | 7 | 66.42 | 67 |
| Gastric cancer | 8 | 59.26 | 59 |
| Gastric cancer | 9 | 28.27 | 28 |
| Gastric cancer | 10 | 43.86 | 44 |
| Gastric cancer | 11 | 26.66 | 27 |
| Gastric cancer | 12 | 45.25 | 45 |
| Gastric cancer | 13 | 11.65 | 12 |
| Gastric cancer | 14 | 69.93 | 70 |
| Gastric cancer | 15 | 52.2 | 52 |
| Gastric cancer | 16 | 24.18 | 24 |
| Gastric cancer | 17 | 47.11 | 47 |
| Gastric cancer | 18 | 32.12 | 32 |
| Colon cancer | 1 | 55.71 | 56 |
| Colon cancer | 2 | 49.45 | 49 |
| Colon cancer | 3 | 53.68 | 54 |
| Colon cancer | 4 | 37.44 | 37 |
| Colon cancer | 5 | 66.04 | 66 |
| Colon cancer | 6 | 59.88 | 60 |
| Colon cancer | 7 | 49.28 | 49 |
| Colon cancer | 8 | 68.98 | 69 |
| Colon cancer | 9 | 34.22 | 34 |
| Colon cancer | 10 | 42.46 | 42 |
| Colon cancer | 11 | 68.69 | 69 |
| Colon cancer | 12 | 72.94 | 73 |
| Colon cancer | 13 | 49.85 | 50 |
| Colon cancer | 14 | 53.44 | 53 |
| Colon cancer | 15 | 35.71 | 36 |
| Colon cancer | 16 | 26.83 | 27 |
| Colon cancer | 17 | 52.51 | 53 |
| Colon cancer | 18 | 16.49 | 16 |
| Colon cancer | 19 | 34.48 | 34 |
| Colon cancer | 20 | 45.63 | 46 |
| Lung cancer | 1 | 42.67 | 43 |
| Lung cancer | 2 | 32.41 | 32 |
| Lung cancer | 3 | 54.08 | 54 |
| Lung cancer | 4 | 58.84 | 59 |
| Lung cancer | 5 | 71.35 | 71 |
| Lung cancer | 6 | 51.87 | 52 |
| Lung cancer | 7 | 55.21 | 55 |
| Lung cancer | 8 | 44.85 | 45 |
| Lung cancer | 9 | 58.6 | 59 |
| Lung cancer | 10 | 31.15 | 31 |
| Lung cancer | 11 | 33.44 | 33 |
| Lung cancer | 12 | 63.79 | 64 |
| Lung cancer | 13 | 61.5 | 62 |
| Lung cancer | 14 | 52.82 | 53 |
| Lung cancer | 15 | 60.76 | 61 |
| Lung cancer | 16 | 13.57 | 14 |
| Lung cancer | 17 | 9.15 | 9 |
| Lung cancer | 18 | 64.61 | 65 |
| Breast cancer | 1 | 60.5 | 60 |
| Breast cancer | 2 | 73.15 | 73 |
| Breast cancer | 3 | 76.87 | 77 |
| Breast cancer | 4 | 84.56 | 85 |
| Breast cancer | 5 | 85.05 | 85 |
| Breast cancer | 6 | 113.07 | 113 |
| Breast cancer | 7 | 109.6 | 110 |
| Breast cancer | 8 | 88.15 | 88 |
| Breast cancer | 9 | 62.98 | 63 |
| Breast cancer | 10 | 111.52 | 112 |
| Breast cancer | 11 | 90.07 | 90 |
| Breast cancer | 12 | 95.65 | 96 |
| Breast cancer | 13 | 93.61 | 94 |

TABLE 3-continued

| Sample Type | Sample No. | RNase content (%) | Ratio relative to healthy control group (%) |
|---|---|---|---|
| Breast cancer | 14 | 102.47 | 102 |
| Breast cancer | 15 | 84 | 84 |
| Breast cancer | 16 | 77.06 | 77 |
| Breast cancer | 17 | 92.55 | 93 |

TABLE 3-continued

| Sample Type | Sample No. | RNase content (%) | Ratio relative to healthy control group (%) |
|---|---|---|---|
| Breast cancer | 18 | 90.32 | 90 |
| Breast cancer | 19 | 94.29 | 94 |

What is claimed is:

1. A double-stranded nucleic acid which can be cleaved by ribonuclease,
    wherein the length of the double-stranded nucleic acid is 7-30 base pairs,
    the base sequence of the first single strand of the double-stranded nucleic acid contains at least one CA base sequence or UA base sequence, the base sequence of the second single strand of the double-stranded nucleic acid contains UG base sequence or UA base sequence which is complementary to the CA base sequence or the UA base sequence in the first single strand,
    one end of the double-stranded nucleic acid is attached to an fluorescence donor group, the other end the double-stranded nucleic acid is attached to an fluorescence acceptor group, and energy transfer can occur between the fluorescence donor group and the fluorescence acceptor group.

2. The double-stranded nucleic acid according to claim 1, wherein the length of the double-stranded nucleic acid is 7, 8, 9, 10, 11, 12, 13, 14, 15, 16, 17, 18, 19, 20 or 21 base pairs.

3. The double-stranded nucleic acid according to claim 1, wherein the first single strand and the second single strand of the double-stranded nucleic acid are perfectly complementary, and the base sequence of the first single strand is 5'-AUGAGCCUGAUUU (SEQ ID NO: 15), 5'-AUGAGCCUAAUUU (SEQ ID NO: 16), 5'-GGCUGCU (SEQ ID NO: 17), 5'-GAAUGAGCU (SEQ ID NO: 18), 5'-GAGUCAGCUAAUCUU (SEQ ID NO: 19) or 5'-UGGUAUGAGCCUGAUUUUGAU (SEQ ID NO: 20).

4. The double-stranded nucleic acid according to claim 1, wherein the double-stranded nucleic acid contains at least one deoxyribonucleotide group.

5. The double-stranded nucleic acid according to claim 1, wherein the double-stranded nucleic acid contains at least one modified nucleotide group.

6. The double-stranded nucleic acid according to claim 5, wherein the modified nucleotide group is a nucleotide group in which at least one of phosphate group, ribose group and base is modified.

7. The double-stranded nucleic acid according to claim 6, wherein the nucleotide group in which ribose group is modified is a nucleotide group in which 2'-hydroxy of the ribose group is modified.

8. The double-stranded nucleic acid according to claim 7, wherein the nucleotide group in which ribose group is modified is a nucleotide group in which 2'-hydroxy of the ribose group is substituted by methoxy or fluorine.

9. The double-stranded nucleic acid according to claim 1, wherein the fluorescence donor group and the fluorescence acceptor group are located on the same nucleic acid single strand.

10. The double-stranded nucleic acid according to claim 1, wherein the fluorescence donor group and the fluorescence acceptor group are located on different nucleic acid single strands.

11. The double-stranded nucleic acid according to claim 1, wherein the fluorescence acceptor group is a fluorescence quenching group.

12. The double-stranded nucleic acid according to claim 1, wherein the fluorescence donor group is at least one selected from the group consisting of fluorescein group, tetrachlorofluorescein group, hexachlorofluorescein group, rhodamine group, tetramethylrhodamine group, Cy dye group, Texas Red group, Bodipy dye group and Alexa dye group.

13. The double-stranded nucleic acid according to claim 12, wherein the fluorescence donor group is at least one selected from the group consisting of 6-carboxyfluorescein group, 5-tetrachlorofluorescein group, 5-hexachlorofluorescein group, 6-carboxy-x-rhodamine group, indodicarbocyanine group and 6-carboxytetramethylrhodamine group.

14. The double-stranded nucleic acid according to claim 1, wherein the fluorescence acceptor group is at least one selected from the group consisting of nitrogen-substituted xanthene group, 4-(phenyldiazenyl)phenylamine group and 4-(phenyldiazenyl) naphthylamine group.

15. The double-stranded nucleic acid according to claim 14, wherein the fluorescence acceptor group is at least one selected from the group consisting of 4-(4'-dimethylaminophenylazo)benzoic acid group, N,N'-dimethyl-N,N'-diphenyl-4-((5-t-butoxycarbonylaminopentyl)aminocarbonyl) piperidinylsulfonerhodamine group, 4',5'-dinitrofluorescein group, pipecolic acid amide group, 4-[4-nitrophenyldiazinyl]phenylamine group and 4-[4-nitrophenyldiazinyl]naphthylamine group.

16. A ribonuclease detection method, including the following steps:
    1) obtaining the double-stranded nucleic acid according to claim 1;
    2) contacting the double-stranded nucleic acid in step 1) with a test sample, such that the double-stranded nucleic acid can be cleaved by the ribonuclease possibly existing in the test sample;
    3) detecting a product after said contacting in step 2), thereby detecting the ribonuclease in the test sample, or detecting the amount of a cleavage product in the product after said contacting in step 2), thereby detecting the content of the ribonuclease in the test sample,
    wherein the cleavage product or the amount thereof is detected by measuring a fluorescence signal with a specific wavelength emitted by the fluorescence donor group and/or the fluorescence acceptor group attached to both ends of the double-stranded nucleic acid.

17. The detection method according to claim 16, wherein the ribonuclease is at least one selected from the group consisting of RNase I, RNase A and RNase H.

18. The detection method according to claim 16, wherein the test sample is at least one selected from the group consisting of blood, plasma, serum, saliva, tissue fluid and urine sample.

19. The detection method according to claim 16 for tumor detection and/or diagnosis, wherein the tumor is gastric cancer, colon cancer or lung cancer.

20. A ribonuclease detection kit, containing an effective amount of the double-stranded nucleic acid according to claim 1.

21. The kit according to claim 20, wherein the ribonuclease to be detected is at least one selected from the group consisting of RNase I, RNase A and RNase H.

22. A tumor detection kit, characterized in that the kit contains the double-stranded nucleic acid according to claim 1.

* * * * *

```
                              SEQUENCE LISTING

<160> NUMBER OF SEQ ID NOS: 20

<210> SEQ ID NO 1
<211> LENGTH: 13
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid first single strand
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a 6-carboxy-fluorescein (FAM)
      group

<400> SEQUENCE: 1
nugagccuga uuu                                                          13

<210> SEQ ID NO 2
<211> LENGTH: 13
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid second single strand
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a tetramethyl-6-
      carboxyrhodamine (TAMRA) group

<400> SEQUENCE: 2
naaucaggcu cau                                                          13

<210> SEQ ID NO 3
<211> LENGTH: 13
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid first single strand
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a 5-tetrachloro-fluorescein
      (TET) group

<400> SEQUENCE: 3
nugagccuaa uuu                                                          13

<210> SEQ ID NO 4
<211> LENGTH: 13
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid second single strand
```

```
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a tetramethyl-6-
      carboxyrhodamine (TAMRA) group

<400> SEQUENCE: 4
naauuaggcu cau                                                          13

<210> SEQ ID NO 5
<211> LENGTH: 7
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid first single strand
<220> FEATURE:
<221> NAME/KEY: misc_feature
<222> LOCATION: (1)..(1)
<223> OTHER INFORMATION: n is g, i.e., guanine ribonucleotide, and the
      5'-end of the ribose is attached to a 5-hexachloro-fluorescein
      (HEX) group

<400> SEQUENCE: 5 ngcugcu                                                                  7

<210> SEQ ID NO 6
<211> LENGTH: 7
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid second single strand
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a tetramethyl-6-
      carboxyrhodamine (TAMRA) group

<400> SEQUENCE: 6 ngcagcc                                                                  7

<210> SEQ ID NO 7
<211> LENGTH: 9
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid first single strand
<220> FEATURE:
<221> NAME/KEY: misc_feature
<222> LOCATION: (1)..(1)
<223> OTHER INFORMATION: n is g, i.e., guanine ribonucleotide, and the
      5'-end of the riboseis attached to a 6-carboxy-fluorescein (FAM)
      group

<400> SEQUENCE: 7 naaugagcu                                                                9

<210> SEQ ID NO 8
<211> LENGTH: 9
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid second single strand
<220> FEATURE:
<221> NAME/KEY: misc_feature
<222> LOCATION: (1)..(1)
```

```
<223> OTHER INFORMATION: n is a, i.e., adenine ribonucleotide, and the
      5'-end of the ribose is attached to a tetramethyl-6-
      carboxyrhodamine (TAMRA) group

<400> SEQUENCE: 8 ngcucauuc                                                                  9

<210> SEQ ID NO 9
<211> LENGTH: 15
<212> TYPE: DNA
<213> ORGANISM: Artificial sequence
<220> FEATURE:
<223> OTHER INFORMATION: Description of Artificial Sequence: Synthetic
      oligonucleotide, Double-stranded nucleic acid first single strand
<220> FEATURE:
<221> NAME/KEY: misc_feature
<222> LOCATION: (1)..(1)
<223> OTHER INFORMATION: n is g, i.e., guanine ribonucleotide, and the
      5'-end of the ribose is attached to a 5-hexachloro-fluorescein
      (HEX) group
<220> FEATURE:
<221> NAME/KEY: misc_feature
<222> LOCATION: (2)..(11)
<223> OTHER INFORMATION: The nucleotides from the 2nd position to the
      11th position are all ribonucleotides
<220> FEATURE:
<221> NAME/KEY: misc_feature
<222> LOCATION: (12)..(12)
<223> OTHER INFORMATION: The nucleotide at the 12th position is a
      deoxyribonucleotide
<220> FEATURE:
<221> NAME/KEY: misc_feature
<222> LOCATION: (12)..(12)
<223> OTHER INFORMATION: The nucleotide at the 12th position is a
      deoxyribonucleotide
<220> FEATURE:
<221> NAME/KEY: misc_feature
<222> LOCATION: (13)..(14)
<223> OTHER INFORMATION: The nucleotides at the 13rd position and the
      14th position are both ribonucleotides

<400> SEQUENCE: 9
nagucagcua atcuu                                                          15

<210> SEQ ID NO 10
<211> LENGTH: 15
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid second single strand
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a tetramethyl-6-
      carboxyrhodamine (TAMRA) group

<400> SEQUENCE: 10
nagauuagcu gacuc                                                          15

<210> SEQ ID NO 11
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid first sine strand
<220> FEATURE:
<221> NAME/KEY: misc_feature
<222> LOCATION: (1)..(1)
<223> OTHER INFORMATION: n is u, i.e., uracil ribonucleotide, and the
      5'-end of the ribose is attached to a 5-tetrachloro-fluorescein
```

```
            (TET) group
<220> FEATURE:
<221> NAME/KEY: misc_feature
<222> LOCATION: (3)..(3)
<223> OTHER INFORMATION: n is g, i.e., guanine ribonucleotide, and the
      2'-hydroxy of the ribose is substituted by methoxy

<400> SEQUENCE: 11
ngnuaugagc cugauuuuga u                                              21

<210> SEQ ID NO 12
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid second single strand
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a tetramethyl-6-
      carboxyrhodamine (TAMRA) group
<220> FEATURE:
<221> NAME/KEY: misc_feature
<222> LOCATION: (14)..(14)
<223> OTHER INFORMATION: n is u, i.e., uracil ribonucleotide, and the
      2'-hydroxy of the ribose is substituted by fluorine

<400> SEQUENCE: 12
nucaaaauca ggcncauacc a                                              21

<210> SEQ ID NO 13
<211> LENGTH: 30
<212> TYPE: RNA
<213> ORGANISM: Artificial sequence
<220> FEATURE:
<223> OTHER INFORMATION: Description of Artificial Sequence: Synthetic
      oligonucleotide, Double-stranded nucleic acid first single strand
<220> FEATURE:
<221> NAME/KEY: misc_feature
<222> LOCATION: (1)..(1)
<223> OTHER INFORMATION: n is a, i.e., adenine ribonucleotide, and the
      5'-end of the ribose is attached to a 6-carboxy-fluorescein (FAM)
      group
<220> FEATURE:
<221> NAME/KEY: misc_feature
<222> LOCATION: (20)..(20)
<223> OTHER INFORMATION: n is c, i.e., cytosine ribonucleotide, and the
      2'-hydroxy of the ribose is substituted by methoxy

<400> SEQUENCE: 13
ngcugguggu acagaugaun uugcaucguc                                     30

<210> SEQ ID NO 14
<211> LENGTH: 30
<212> TYPE: DNA
<213> ORGANISM: Artificial sequence
<220> FEATURE:
<223> OTHER INFORMATION: Description of Artificial Sequence: Synthetic
      oligonucleotide, Double-stranded nucleic acid second single strand
<220> FEATURE:
<221> NAME/KEY: misc_feature
<222> LOCATION: (1)..(1)
<223> OTHER INFORMATION: n is g, i.e., guanine ribonucleotide, and the
      5'-end of the ribose is attached to a tetramethyl-6-
      carboxyrhodamine (TAMRA) group
<220> FEATURE:
<221> NAME/KEY: misc_feature
<222> LOCATION: (6)..(6)
<223> OTHER INFORMATION: The nucleotide at the 6th position is a
      deoxyribonucleotide
```

```
<400> SEQUENCE: 14
nacgatgcaa gaucaucugu accaccagcu                                          30

<210> SEQ ID NO 15
<211> LENGTH: 13
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 15
augagccuga uuu                                                            13

<210> SEQ ID NO 16
<211> LENGTH: 13
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 16
augagccuaa uuu                                                            13

<210> SEQ ID NO 17
<211> LENGTH: 7
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 17 ggcugcu                                                                   7

<210> SEQ ID NO 18
<211> LENGTH: 9
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 18 gaaugagcu                                                                 9

<210> SEQ ID NO 19
<211> LENGTH: 15
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 19
gagucagcua atcuu                                                          15

<210> SEQ ID NO 20
<211> LENGTH: 21
<212> TYPE: RNA
<213> ORGANISM: Artificial sequence
```

-continued

```
<220> FEATURE:
<223> OTHER INFORMATION: Description of Artificial Sequence: Synthetic
      oligonucleotide

<400> SEQUENCE: 20
ugguaugagc cugauuuuga u                                                  21
```